United States Patent
Reineccius et al.

(10) Patent No.: US 9,861,028 B2
(45) Date of Patent: Jan. 9, 2018

(54) SEED TREATMENT DEVICE WITH IMPROVED FLUID APPLICATION

(71) Applicant: Bayer CropScience LP, Research Triangle Park, NC (US)

(72) Inventors: Greg A. Reineccius, Shakopee, MN (US); Ron Reichert, Cary, NC (US)

(73) Assignee: Bayer CropScience, LP, Research Triangle Park, NC (US)

( * ) Notice: Subject to any disclaimer, the term of this patent is extended or adjusted under 35 U.S.C. 154(b) by 0 days.

(21) Appl. No.: 15/210,288

(22) Filed: Jul. 14, 2016

(65) Prior Publication Data

US 2017/0094892 A1    Apr. 6, 2017

Related U.S. Application Data

(63) Continuation of application No. 13/864,132, filed on Apr. 16, 2013, now abandoned.

(60) Provisional application No. 61/624,668, filed on Apr. 16, 2012.

(51) Int. Cl.
*A01C 1/06* (2006.01)
*B05B 3/02* (2006.01)
*B05B 3/10* (2006.01)

(52) U.S. Cl.
CPC ............. *A01C 1/06* (2013.01); *B05B 3/105* (2013.01); *Y10S 118/16* (2013.01)

(58) Field of Classification Search
None
See application file for complete search history.

(56) References Cited

U.S. PATENT DOCUMENTS

| | | | |
|---|---|---|---|
| 4,217,851 A | | 8/1980 | Biehl et al. |
| 4,465,017 A | | 8/1984 | Simmons |
| 4,554,887 A | * | 11/1985 | Yoakam .......... A23G 3/26 118/666 |
| 4,657,773 A | * | 4/1987 | Mueller .......... A01C 1/00 118/303 |
| 4,689,249 A | | 8/1987 | Thygesen |
| 4,987,850 A | | 1/1991 | McCracken |
| 5,108,034 A | | 4/1992 | Huey et al. |
| 5,370,734 A | * | 12/1994 | Ferrero .......... A21C 15/002 118/13 |
| 5,567,238 A | | 10/1996 | Long, Jr. et al. |
| 5,718,769 A | | 2/1998 | Hashizume et al. |
| 5,891,246 A | * | 4/1999 | Lund .......... A01C 1/06 118/13 |

(Continued)

FOREIGN PATENT DOCUMENTS

DE    4128258 A1    11/1993
DE    4411058 A     10/1995

(Continued)

*Primary Examiner* — Binu Thomas

(57) ABSTRACT

A seed treater provides enhanced seed coating capabilities and performance. The seed and/or treatment fluid may be heated for improving vaporization and absorption by the seed. Air may be injected in the seed treater to provide heat, dehumidified air, and to provide vaporization enhancement, and component cleaning functions. The functions may be controlled by a control processor based on recipes and may be changed dependent upon sensed or input environmental conditions such as temperature and humidity.

17 Claims, 6 Drawing Sheets

(56) References Cited

U.S. PATENT DOCUMENTS

Figure 1A:
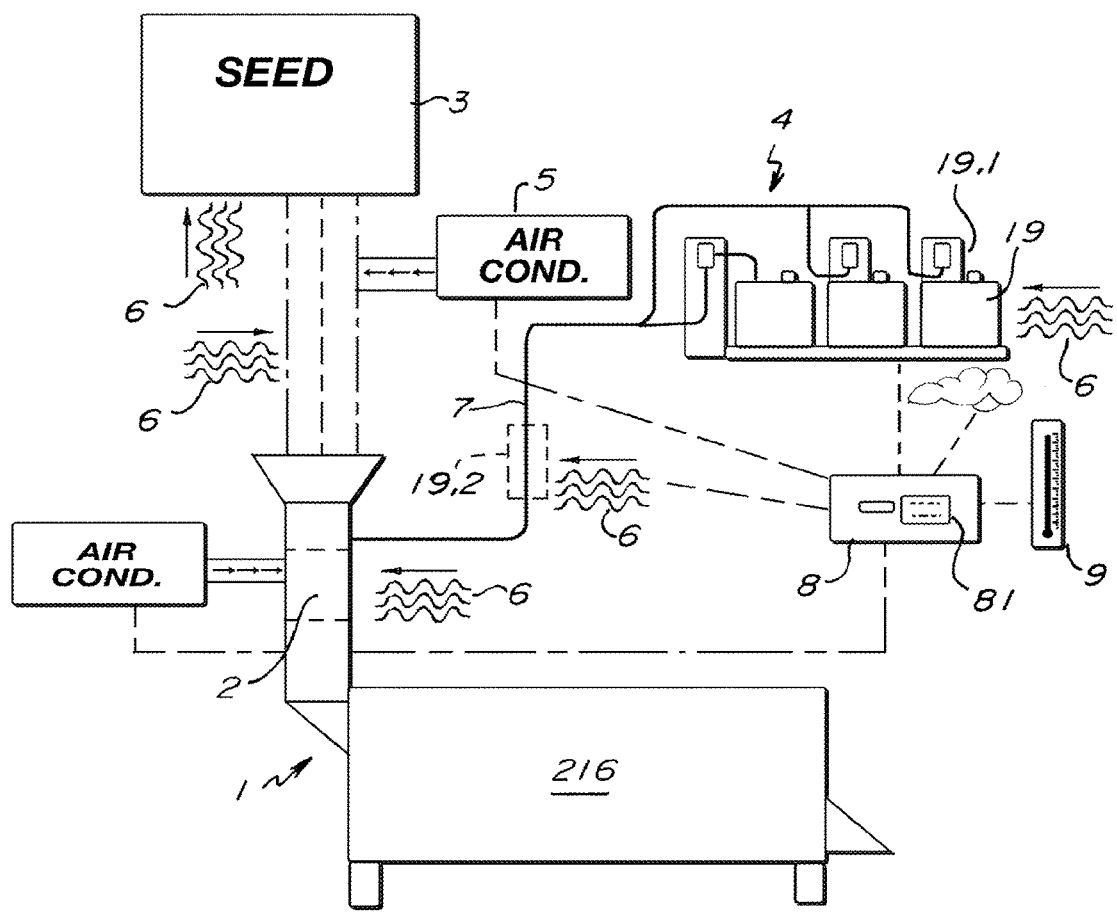

| | | |
|---|---|---|
| 6,202,346 B1 | 3/2001 | Lyons et al. |
| 6,582,516 B1 | 6/2003 | Carlson |
| 2001/0016224 A1 | 8/2001 | Huttlin |
| 2001/0043966 A1 | 11/2001 | Delrue et al. |
| 2006/0236925 A1 | 10/2006 | Lund |
| 2011/0027479 A1 | 2/2011 | Reineccius et al. |

FOREIGN PATENT DOCUMENTS

| | | |
|---|---|---|
| WO | 3736471 A1 | 10/1997 |
| WO | 2011017252 A1 | 2/2011 |
| WO | 2012078918 A2 | 6/2012 |
| WO | 2012078928 A2 | 6/2012 |

\* cited by examiner

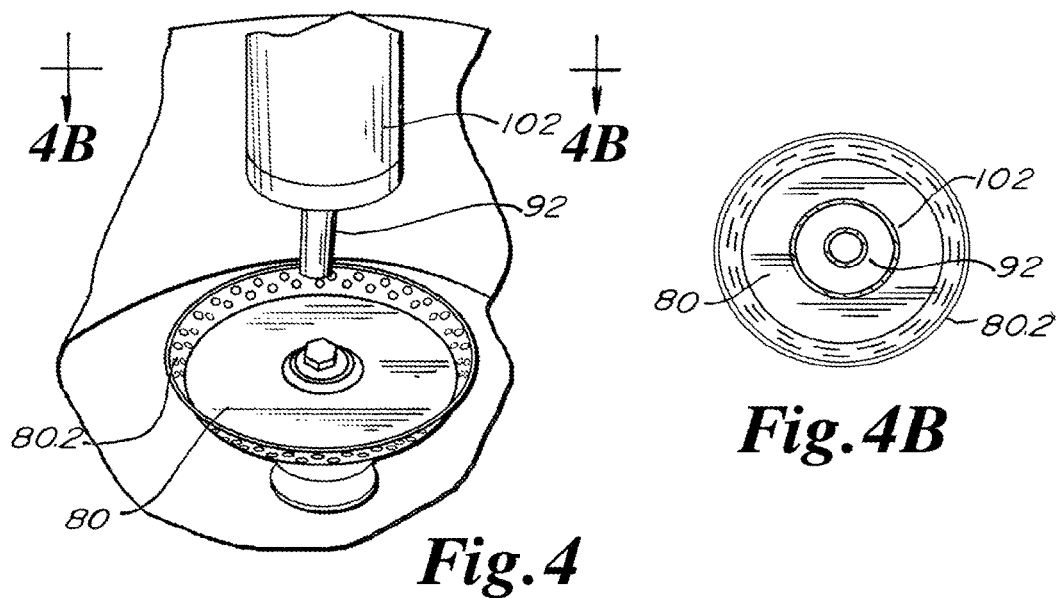
Fig.4
Fig.4B
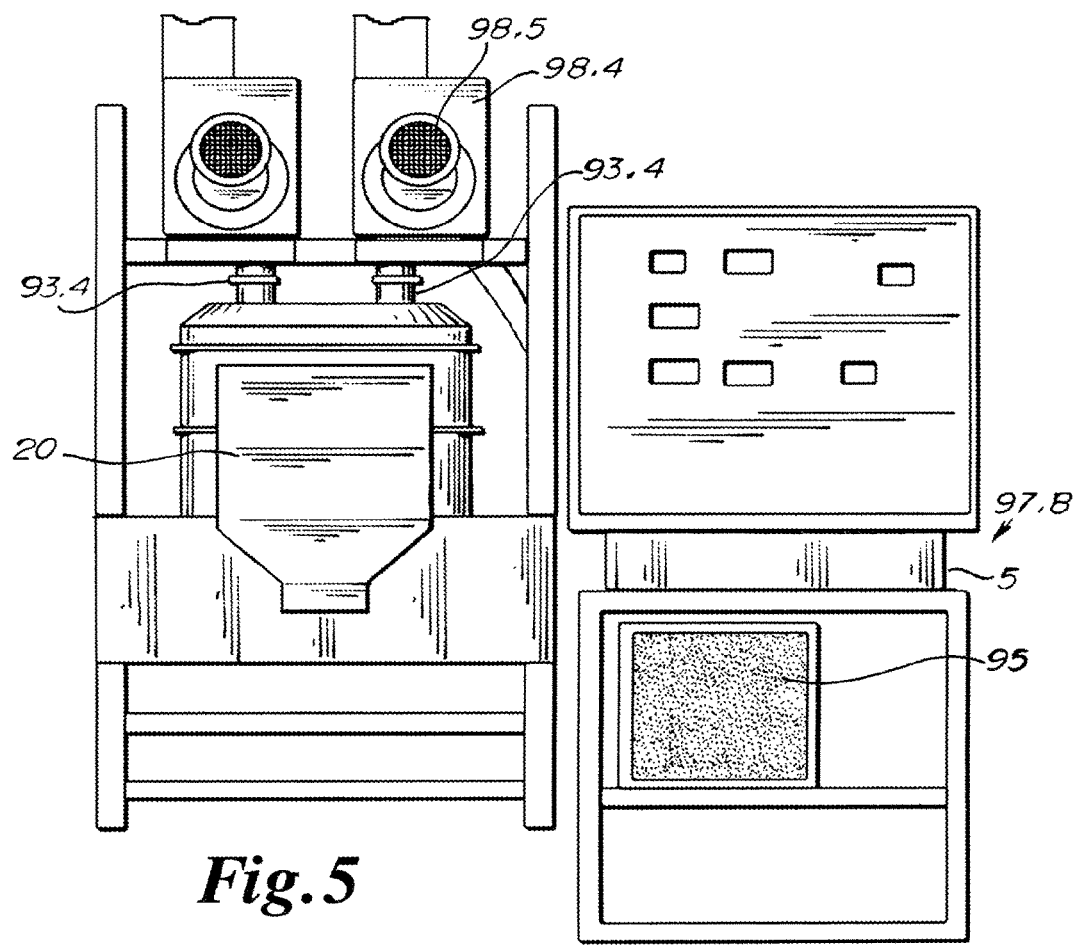
Fig.5

SEED TREATMENT DEVICE WITH IMPROVED FLUID APPLICATION

CROSS-REFERENCE TO RELATED APPLICATIONS

The present application is a continuation of U.S. patent application Ser. No. 13/864,132, filed on Apr. 16, 2013, which claims the benefit of U.S. Provisional Patent App. No. 61/624,668, filed Apr. 16, 2012, all of which are incorporated herein by reference in their entireties.

FIELD OF THE INVENTION

The present invention generally relates to an apparatus for surface treatment of seeds. More particularly, the present invention relates to a device for surface treatment of seeds having an improved fluid application means.

BACKGROUND OF THE INVENTION

Seeds that are planted for agricultural and other purposes are often treated prior to planting. The treatments may accomplish many different purposes including deterrence or prevention of insect and other animal pests that would target sown or newly germinated seed for attack. These animals may directly cause damage to the seed or may introduce one or more pathogens, including viruses, directly into the seed. Treatments may also target bacteria, molds and fungus that have contaminated seeds or that are known to be present in the soil in which the seeds will be planted. Direct application of seed treatment allows for a reduction in the amount of treatment composition that would be required by application to soil after planting. Also, post-planting application may not penetrate the soil to a level or location where it would be effective.

Treatment of seeds, however, involves applications of chemicals and other agents that are expensive and may even be toxic to the seeds on which they are applied. The amount of treatment composition is also necessarily small and often provides protection or other advantage for only a short period of time after planting. However, in a number of situations, the advantages of treatment with one or more compositions will outweigh the disadvantages. These situations include the use of rare or expensive seed, the use of older seed or seed with low germination rates, the use of seed known to be contaminated or infested, the use of seed known to have been produced in conditions likely to lead to contamination or infestation, and the use of seed in fields known to be prone to contamination or infestation.

Various devices for treatment of seeds in batch or continuous treatment mode are known. U.S. Pat. No. 5,891,246 to Lund, the disclosure of which is hereby incorporated by reference, describes a seed coating apparatus for applying a coating fluid whereby seeds are dispersed with a seed dispersing member.

U.S. Pat. No. 4,657,773 to Mueller, the disclosure of which is hereby incorporated by reference, describes a process and apparatus for dressing seed in which seed is guided over a dispensing cone through a jet of dressing and onto a rotary table.

DE 4411058 to Niklas, the disclosure of which is hereby incorporated by reference, describes a device with a mixing bowl connected to a high speed, multi-turn actuator and a mechanism to feed seed into the mixing bowl. The bowl rotates to rotate seed being treated therein. The seed treating formulation is sprayed in the bowl while the seed is being rotated to uniformly coat the seed with the formulation.

SUMMARY OF THE INVENTION

The apparatus of the invention is directed toward an apparatus for surface treatment of seeds. Treatment apparatus according to the invention can treat seeds continuously or in batches. Treatment fluid is delivered into a treatment area of system by a fluid communication line and distributed onto seeds such as via rotation of an atomizer wheel configured as a centrifugal apertured plate. Means are provided to increase the absorption and/or adhesion and/or drying time of the treatment fluid with seed being treated. In embodiments of the invention, means are provided to enhance the vaporization of the treatment fluid. In embodiments heat is added to the treatment region of the seed. In certain embodiments, conditioned air may be heated and/or dehumidified and provided into the seed treatment apparatus at, for example, the fluid application region. The conditioned air may be provided to the seed or seed stream prior to fluid application region. In embodiments, conditioned air includes dehumidified air to enhance the vaporization of the treatment fluid. In an embodiment the treatment fluid temperature is altered.

In embodiments of the invention, heated air is directed at the centrifugal plate with an air delivery duct. In such embodiments, the air delivery tube delivering the heated air may surround the fluid flow line delivering the treatment fluid to the fluid application region. The heated air flow also warms the fluid in the fluid flow line. In certain embodiments, the fluid may be more directly heated with a dedicated heat source, such as electric heating elements, applied directly to a treatment fluid reservoir or to a fluid line in or going to the seed treater. Heating of the fluid may occur prior to the commencement of the seed treatment and/or during the seed treatment. In certain embodiments, the fluid may be heated to a particular temperature for treatment before dispersion. In certain embodiments, the fluid may be heated from ambient to a particular temperature or temperature differential prior to application to the seeds. In certain embodiments, particular components of seed treater may be heated, that is, for example, a treatment bowl or centrifugal plate. This may provide reduced viscosity of fluid in contact with the component as well as lowering the vapor pressure of the fluid. In embodiments, the seed is warmed prior to or during application of the fluid. In certain embodiments, the air may be injected within the seed stream flow ahead of the region where the seeds are treated effectively warming the seeds before treatment. In other embodiments, the seeds may be preheated by other means, such as heating the seed containment.

In embodiments of the invention, such heating and/or air conditioning as described above, may be automatically controlled and may be part of treatment recipes provided to a process controller controlling the equipment. In embodiments, the heating and/or air conditioning as described above, may be automatically controlled based upon existing environmental conditions. For example, if an ambient temperature is below 50 degrees Fahrenheit, the seed stream may be warmed, and/or the treatment fluid may be warmed to a desired temperature suitable for optimal seed treatment.

A feature and advantage of embodiment of the invention is optimally controlling the evaporative properties within a seed treater to maximize seed treatment efficacy and minimize treatment time.

A feature and advantage of embodiments of the invention is enhanced seed coating, in particular, more uniform thorough coating in less time. Additionally, a feature and advantage of embodiments of the invention is less dust generation.

A feature and advantage of particular embodiments of the present invention where air is injected into the top side of the mixing bowl is improved dispersion of treatment fluid. Air is blasted from the air delivery tube into the centrifugal plate as the plate is spinning providing enhanced dispersion of the treatment fluid. The combination of the blowing air with the spinning plate functions to increase the atomization of the fluid particles, which provides better fluid dispersal from the atomizer. Providing heated and/or dehumidified air can further enhance the vaporization of the treatment fluid.

Another feature and advantage of embodiments of the present invention is enhanced treatment fluid absorption on the seeds. By heating the fluid, for example inline with the air delivery tube surrounding the fluid communication line and at the centrifugal plate, the viscosity and vapor pressure of the fluid is lowered. As such, when the fluid is dispersed from the atomizer and contacts the seeds, the fluid is more readily absorbed and retained on the surface of the seeds.

Another feature of embodiments of the invention is the injection of the conditioned air circumferentially inside a containment housing for a mixing bowl. In embodiments the air is injected in a radial direction at the top of the bowl containment. In an embodiment the air outlet port is radially outward and downward, in an embodiment the air is directed circumferentially to correspond with the rotation of the seed in the rotating bowl.

A further feature and advantage of embodiments of the present invention is a cleaner fluid treatment bowl and centrifugal plate. Due to the enhanced dispersion of the warmed fluid, the increased absorption of the fluid by the seeds, and the air-scrubbing of the components, such as the spinning centrifugal plate, a greater percentage of fluid remains with the seeds. There is therefore less buildup of leftover fluid within the treatment area, resulting in cleaner post-treatment equipment.

Another feature and advantage of embodiments of the present invention is a reduced amount of time to treat a batch of seeds. Increased dispersal of treatment fluid and absorption of fluid by the seeds means that the seeds need to spend less time being treated to obtain the same or better level of treatment. As such, each batch can be processed more quickly, which leads to increased seed capacity for the particular apparatus and the plant utilized the apparatus as well as the ability to apply addition seed treatments.

Another feature and advantage of embodiments of the present invention is reduced treated seed dust levels. Application of heated or unheated air during treatment fluid application allows for increased application rates of polymer based or other dust control seed coating products to provide for better seed treatment adhesion to the seed and or improved durability of the seed treatment to reduce attrition of the treatment during post treatment handling and planting.

BRIEF DESCRIPTION OF THE DRAWINGS

The embodiments of the present invention may be more completely understood in consideration of the following detailed description of various embodiments of the invention in connection with the accompanying drawings, in which:

FIG. 1A is schematic view of a continuous feed seed treatment system according to an embodiment of the present invention.

FIG. 1B is perspective view of a batch seed treatment system according to an embodiment of the present invention.

FIG. 2 is an image of a portion of a seed treatment system according to an embodiment of the present invention.

FIG. 3A is a perspective view of a bowl, dispense portion, and air inlet port of a seed treatment apparatus of a batch treating system according to an embodiment of the present invention.

FIG. 3B is a cross section view of a bowl, dispense portion, and air inlet port as illustrated in FIG. 3A of a seed treatment apparatus according to an embodiment of the present invention.

FIG. 3C is a perspective view of a bowl, dispense portion, and air inlet port of a seed treatment apparatus according to an embodiment of the present invention.

FIG. 4 is a drawing of a liquid dispersion portion of a seed treatment system according to an embodiment of the present invention.

FIG. 4B is a plan view of the dispense portion of a seed treatment system according to an embodiment of the present invention.

FIG. 5 is plan view of a seed treatment system including an air conditioner according to an embodiment of the present invention.

FIG. 6 is a perspective view of a portion of a control processor with an interface and heater unit of a seed treatment apparatus according to an embodiment of the present invention.

FIG. 7 is a side view of a portion of a continuous feed seed treatment system according to an embodiment of the present invention illustrating the seed stream.

While the present invention is amendable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention.

DETAILED DESCRIPTION OF THE INVENTION

FIG. 1*a* shows a schematic figure of a system in accord with the invention. A seed treater 1 has a seed treatment region 2 and with a stock 3 of seeds to be treated, a fluid dispense station 4 providing treatment fluid to the seed treater. Conditioned air may be provided to the seed treater by air conditioning units 5 that may heat and/or dehumidify air. Alternate locations of providing the heated air are illustrated. Such conditioned air can also be provided to the seed treater either at the containment region or as the seed is being conveyed to the seed treater. Heat 6, indicated by the wavy lines, may be provided to the treatment fluid at the dispense station 4, at fluid lines 7 connected to the seed treater, directly to components of the seed treater, such as an internal fluid line. The heat may be provided by electric heating elements 19.1, such as radiant heat or by elements conductively connected to components, for example, electric heating coils. Also the heat 6 may be provided by heated air.

A control processor 8 with operator interface 8.1 can be connected to control all functions of the components and can store and or receive recipes. See co-owned applications Nos. WO 2012/078928 and WO 2012/078918 that are hereby incorporated by reference herein. The control processor and other equipment can be connected to the internet and remote locations with the functionalities and capabilities as described in these two co-owned application. The control processor 8 can be connected to sensors 9 that can sense environmental conditions, such as temperature and humidity, and change the operating characteristics/parameters in accord with preprogrammed or input instructions. For example, when the temperature drops below a certain level, heat or heated air can be provided to the seed treater, and/or treatment fluid, and/or seed. Or, if the humidity is excessive, dehumidified air can be provided.

Figure 1B:
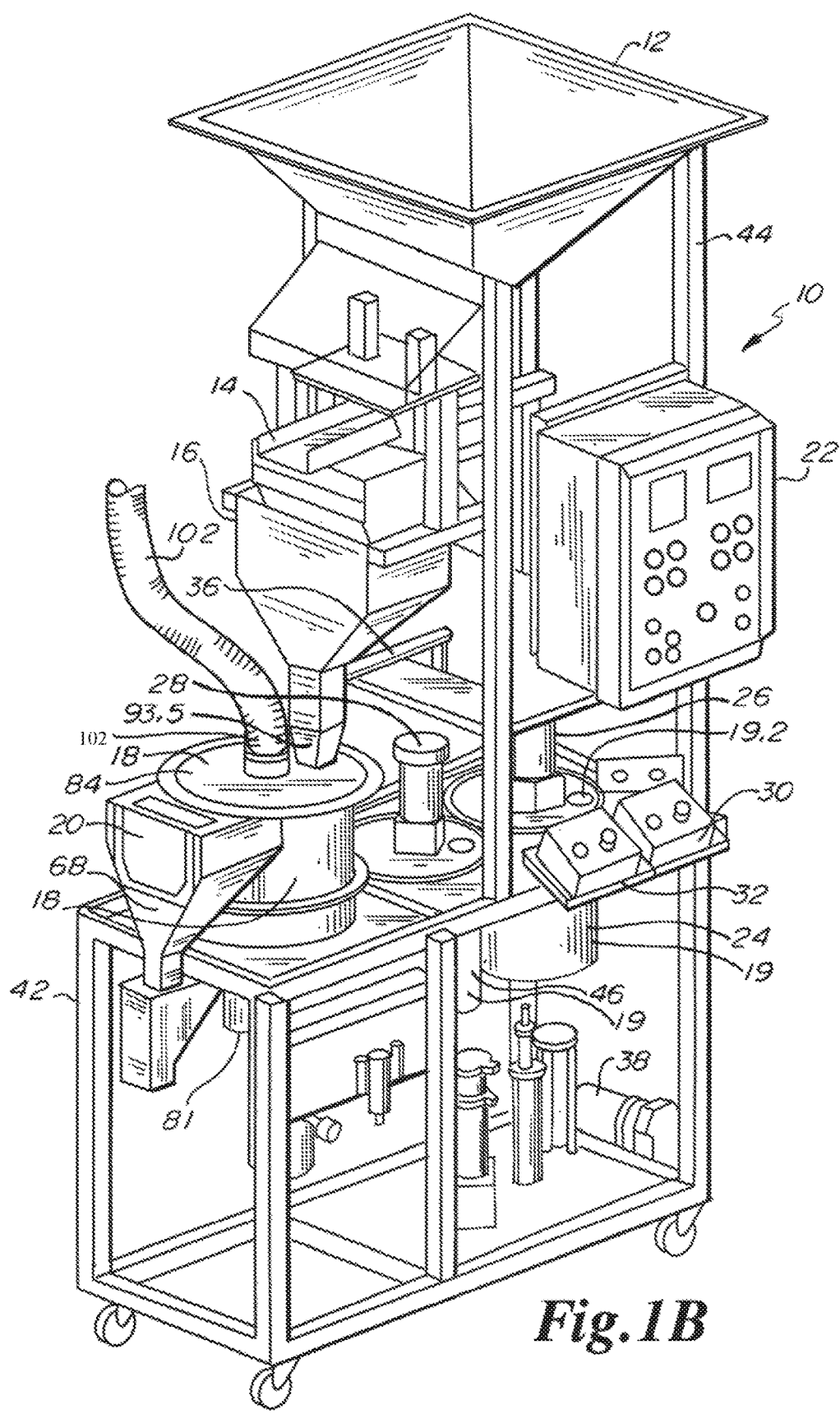
Figure 2:
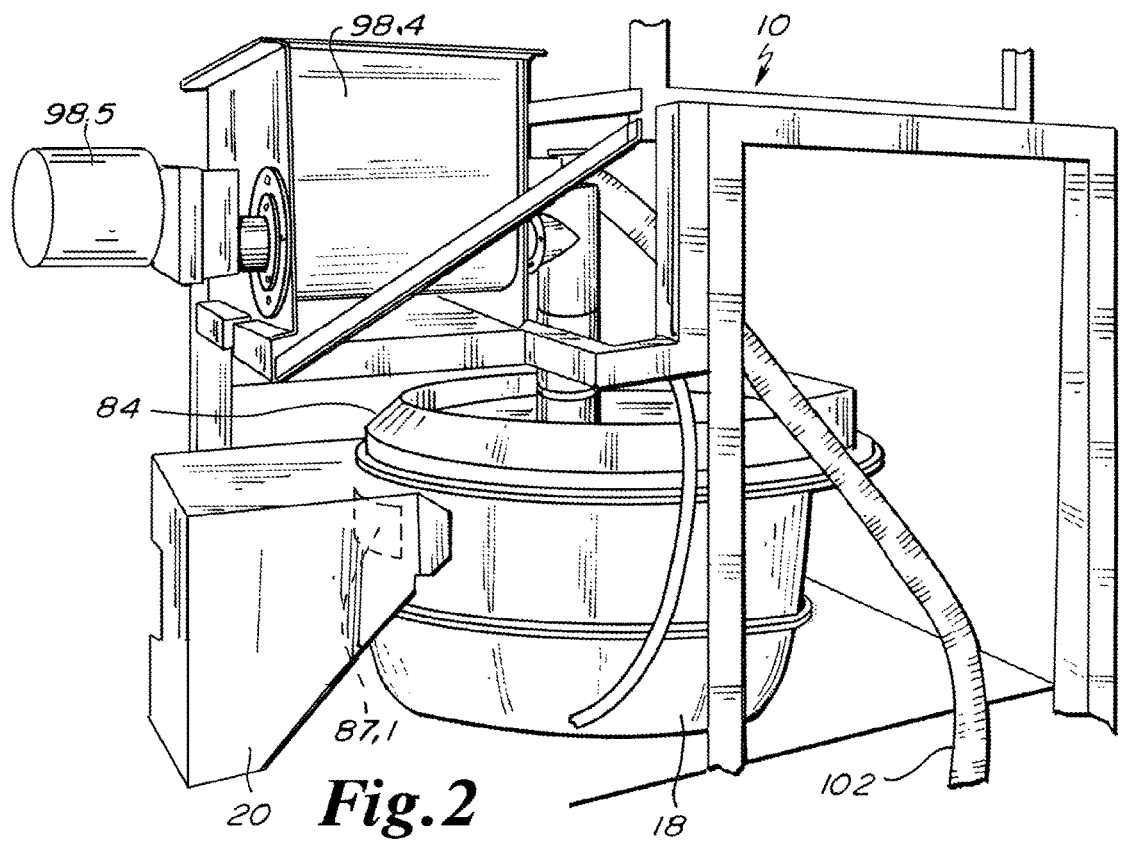

FIG. 1*b* shows a seed treater apparatus 10 according to an embodiment of the present invention that can include an untreated seed hopper 12, scale 14, control panel 22, and conveyance hopper 16. Treatment containment housing container 18 along with discharge hopper 20, premix containers 24, 46, metering pump motor controllers 30, 32, pumps 38, and bowl motor 81 are mounted to a lower frame component 42.

Seed for treatment may be introduced into untreated seed hopper 12 which is mounted at the top of upper frame component 44. Seed contained therein may be dispensed to a scale 14 for weighing and identification of a batch for treatment. Scale 14 may be a manual scale and fed by means of a magnetic or vibratory feeder from untreated seed hopper 12 to scale 14. In the alternative, a load cell may be employed to identify and dispense a batch for treatment. Feed is controlled by control processor 22 to operate until such time as scale 14 indicates to controller 22 that the desired weight has been reached. At this point, feeder is stopped and the batch dispensed to conveyance hopper 16. Conveyance hopper 16 operates to collect the batch identified for treatment and directs the batch to treatment container 18.

Treatment agents for use in the modular seed treatment apparatus of the invention may be prepared in one or more pre-mix containers, which can be reversibly mounted to the frame assembly. The pre-mix containers 24, 46 may each hold up to ten gallons of solution. Fluid treatment reservoirs 19, configured as pre-mix containers 24, 46 may have agitation devices associated with them including a motor 26, 28 deploying a rod with two or more paddles for agitation of liquid contained therein and may also have heaters 19.2. Referring to FIG. 1A, fluid treatment reservoirs 19 configured as drums may have heating units 19.1 and sensors associated therewith to heat the liquid. Additionally heaters 19.2 may be applied to the liquid input line 7.

Figure 3A:
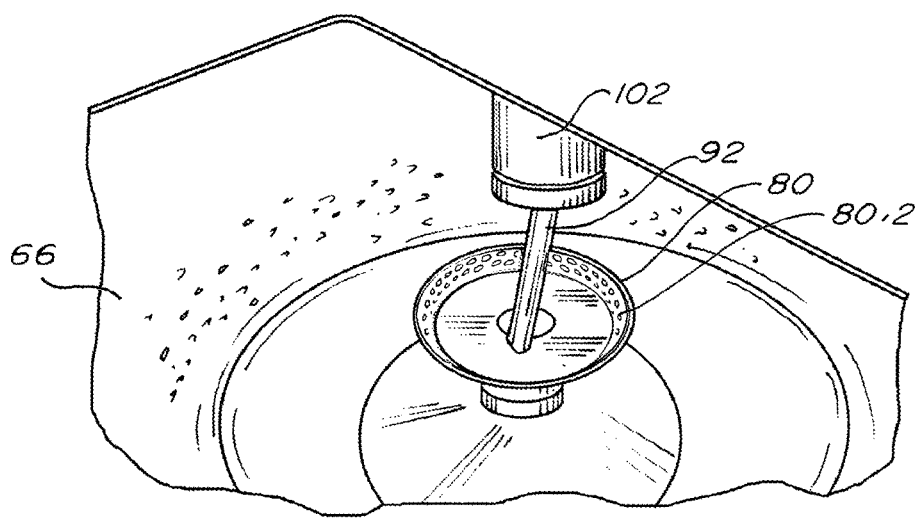
Figure 3B:
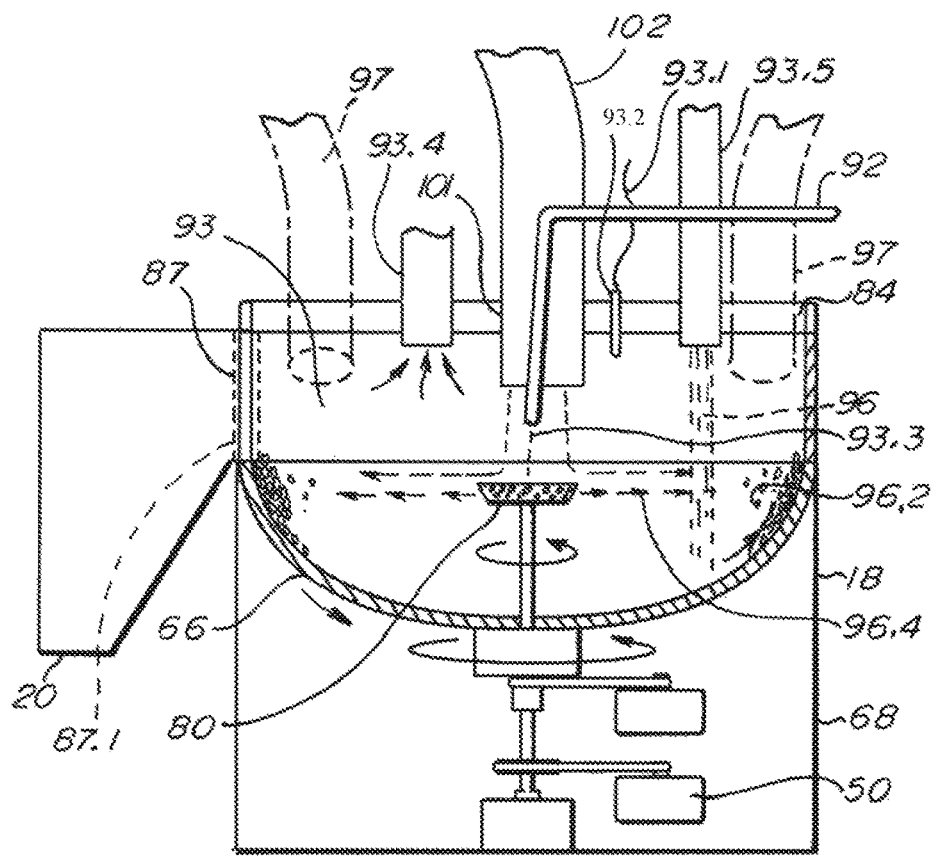

Containment housing 18, as seen in FIGS. 1A, 1B, 2, and 3B includes a body portion 68 and a lid 84. Lid 84 can be secured to body 68 by a mechanical connection including, but not limited to, bolts extending through lid and into a flange on body or clamps. An atomizer comprising a centrifugal plate 80, as shown in FIGS. 3 and 4, is disposed within the interior 93 of treatment container and revolves at high speed to disperse treatment composition. Liquid dispersion portion 80 configured as a centrifugal tray or plate with a cylindrical or frustoconical shaped portion 80.2 extending upwardly is driven by atomizer motor 50. Treatment container 18 can also include fins extending from lid 84 designed to direct seeds entering treatment container 18 and within treatment container toward centrifugal plate 80 and/or bowl 66. Bowl 66 is a seed dispersion portion of the apparatus and is disposed within treatment container 18 and is driven by a bowl motor 81 to rotate in a horizontal plane. Bowl motor is set to operate at speeds sufficient to impart centrifugal force to seeds being treated to drive the seeds toward the wall and upward toward fins and an outlet port 87. Bowl motor is controlled by control processor 8. Seed outlet port may include openable and closeable gate 87.1 which may be manually operated or electrically operated and may be automatic and controlled by control processor 8. Cover or lid 84 also defines one or more openings for traverse of one or more fluid communication lines 92, sensor lines 93.1 for temperature sensors 93.2, and dust discharge ports 93.4, and/or conditioned air outlet ports, and seed input ports 93.5. Seed treatment liquid input line 92 discharges the treatment fluid 93.3 into the liquid dispensing portion or tray 80. Seed 96 enters the interior 93 through the port 93.5 and by way of the seed dispersion portion, the rotating bowl 66, which elevates the seed into an annular seed treatment region 96.2 where the spray 96.4 from the liquid dispersion portion 80 contacts the seed. Exterior blowers 98.4 with motors 98.5 may be used to remove dust and assist in the exit of the conditioned heated air.

The figures illustrate an air inlet port 101 an air delivery conduit or duct 102 that extends from an air conditioner 97.8 to the open interior 93 of the containment housing 18 for injecting conditioned air into the system. In one embodiment, as can be seen in FIGS. 3A, 3B, 4, and 4B, the air delivery duct 102 surrounds the seed treatment liquid input line 92. Air can be delivered through air delivery tube 102 simultaneously as treatment composition is delivered through fluid communication line.

In one embodiment, air is provided by a blower. In another embodiment, the air is provided through a compressed air line with a diffuser. In an embodiment shown in FIGS. 4 and 5, air conditioner including a heater portion 95, the blower 95.2 or compressed air source can be controlled by the control panel 22 of the control processor of device. If the air is to be heated and/or dehumidified prior to directing it to the treatment container 18, the control panel 22 can also contain the heat source. Control panel 22 can include various displays and controls, including, for example, outgoing air temperature, outgoing air relative humidity, incoming air temperature, incoming air relative humidity and seed temperature.

Figure 3C:
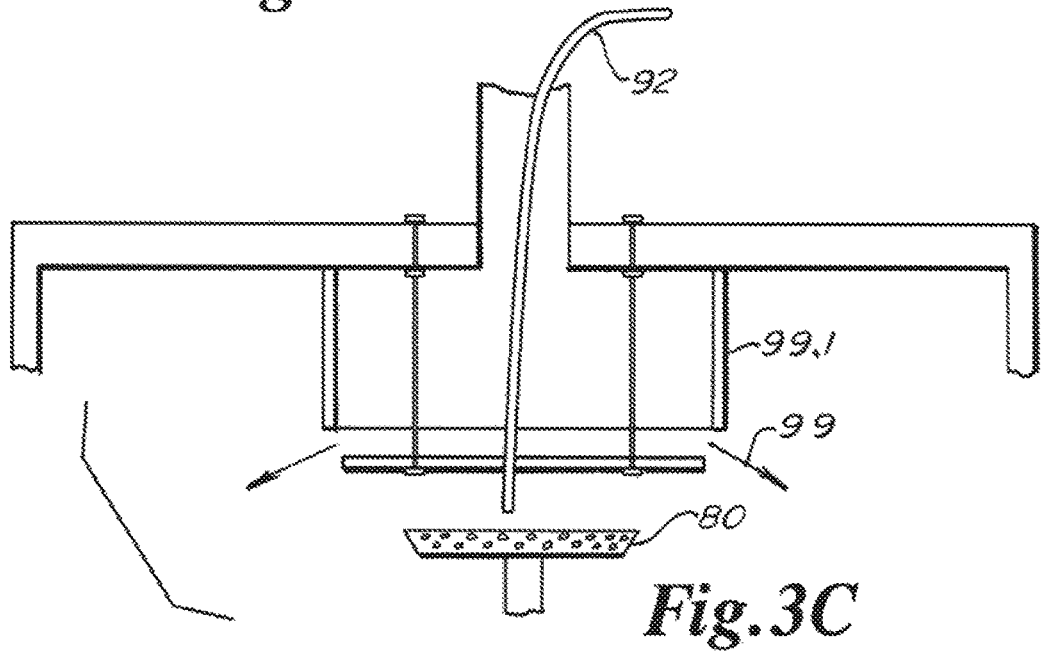
Figure 6:
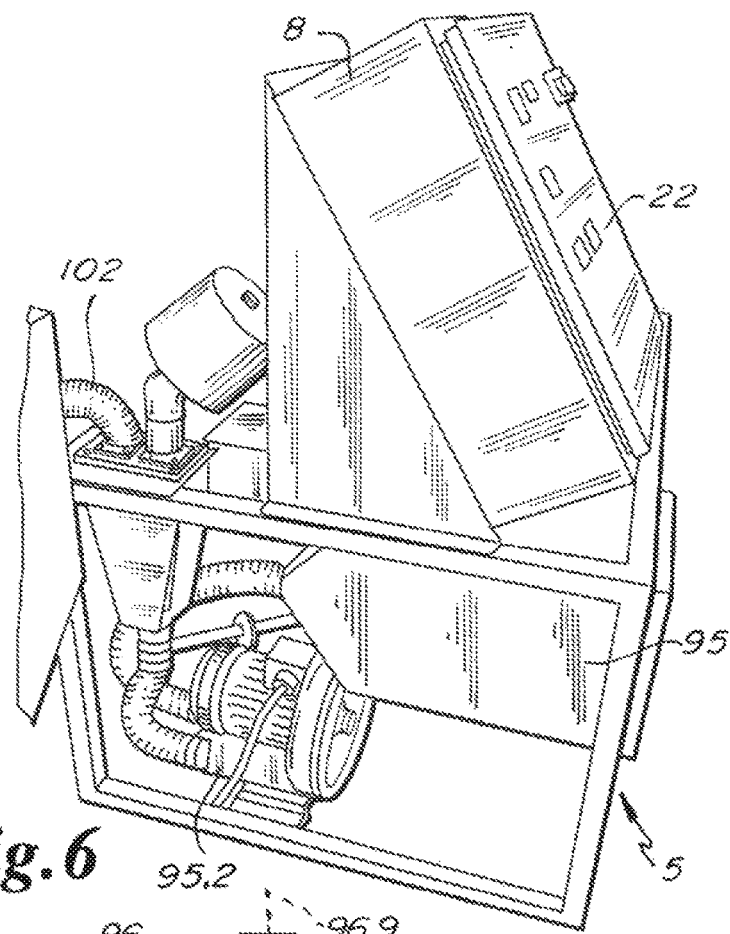

Air provided through air delivery tube 102 can be heated air or non-heated air and/or dehumidified air. Blasting the centrifugal plate 80 with air during the application of treatment fluid provides for better atomization of the fluid particles due to the combination of the spinning plate and the blowing air. Use of air also provides for a cleaner bowl 66 and plate 80 following treatment. Heating the air prior to dispersal can provide additional advantages. As the heated air travels through the air delivery tube 102 simultaneously as the treatment fluid 93.3 travels through the fluid communication line, the heated air elevates the temperature of the fluid in-line. Elevation of the temperature of the fluid causes the viscosity and vapor pressure of the fluid to be lowered, which results in better dispersion of the fluid by the centrifugal plate and better absorption of the fluid by the seeds. In addition, the heated air serves to warm the centrifugal plate 80, which magnifies the beneficial effects of the heated fluid by further heating the fluid. In one embodiment, heated air is provided at 150 degrees Fahrenheit. In other embodiments, about 140 degrees F. In other embodiments, about 130 degrees F. In an alternative embodiment, rather than, or in addition to, providing the air (heated or non-heated) via an air delivery tube 102 surrounding the fluid communication line 92, air can be injected circumferentially from around the side of the bowl 66 as illustrated by the air outlet 97 in FIG. 3B. FIG. 3C illustrates another embodiment where the conditioned/heated air 99 is directed out radially by an air deflector 99.1.

Addition of heated air into system has also been found to reduce the batch time necessary to coat a batch of seeds with treatment fluid and to reduce the amount of dust on treated seeds due to both the effects of the air flow and heat. Reduced application time provides the opportunity for significant advantages, including higher seed plant capacity as well as additional coating to improve dust retention, seed appearance and seed flow.

In one mode of operation, an operator may place a quantity of seed to be separated into batches and treated in place in untreated seed hopper 12. Seed is dispensed by operation of vibratory feeder into scale 14. Pre-mix container 24 is charged with ingredients for the treatment composition and agitator motor 26 is engaged to mix and maintain composition of the treatment composition. A second treatment composition may be prepared by charging a second pre-mix container 46 with ingredients for the second treatment composition and engaging agitator motor 28 to mix and maintain composition of the second treatment composition. When heated air is desired to be introduced into treatment container 18, a heat source and blower associated with the control panel 22 may be activated. Predetermined quantities of seed are then dispensed by scale 14 to conveyance hopper 16. Seed falls into treatment container 18 and falls into bowl 66. Rotation of bowl 66 causes seed to be urged to the outside of the bowl and against the inner side of treatment container 18 as well as upward toward lid 84. Fins direct seed back toward the center of treatment container 18 and down toward bowl 66. Controller 22 operates to introduce treatment composition from one or both pre-mix containers 24,46 by operation of pumps 38, 60 into the treatment space inside treatment container 18 through fluid containment line 92. Simultaneously, heated or unheated air is introduced into treatment container 18 through air delivery tube 102. Seed is then allowed to interact with the one or more treatment compositions for a pre-determined period. Optionally, dry powder may be dispensed from a powder container into the treatment space from a powder conveyer according to the program set in controller 22. A second pre-determined period is allowed to elapse to allow for coating of treated seed with the introduced powder. Controller 22 then directs opening of seed exit gate or door 87.1 and treated seed is directed through collection hopper 20 to packaging equipment or other destinations as desired by the operator. Further details of the features and operation of seed treatment apparatus can be found in United States Patent Application Publication No. 2006/0236925, which is hereby incorporated by reference.

Figure 7:
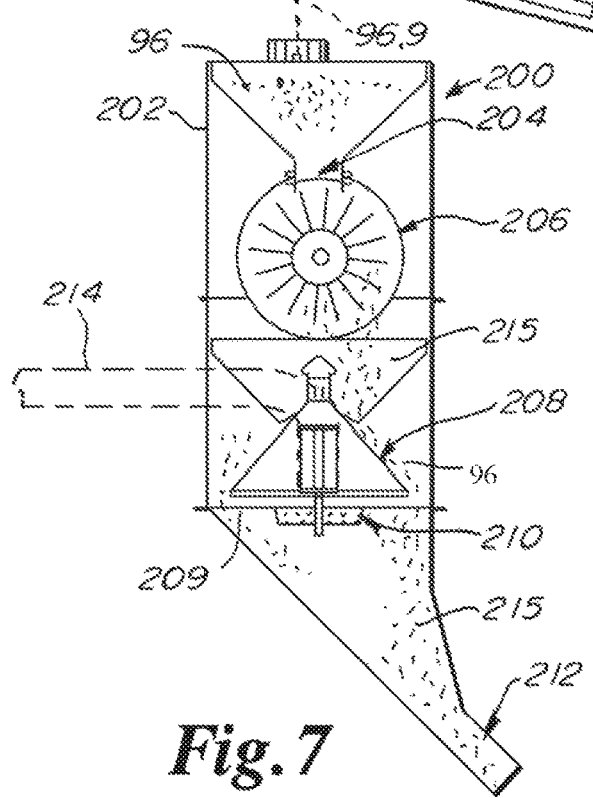

FIGS. 1a and 7 depicts another embodiment of the present invention in a continuous feed seed treatment apparatus 1 wherein heat such as through heated air is introduced into a continuous seed processing apparatus 1. Seed treatment apparatus 1 can include a housing 202 including an seed inlet port 204, a seed wheel 206, a dispersion portion configured as a cone 208 that leads to an annular treatment region 209, an atomizer wheel or centrifugal plate 210, and an outlet 212. Housing outlet 212 can connect to a polishing drum 216 or mixing chamber. The atomizer wheel 210 can be fluidly connected to one or more tanks containing products for treating the seeds via an inlet tube that may be heated. The system can be connected to a computer system 8, a control processor, having a control panel for monitoring and/or adjusting the system. The system 1 can further include an air delivery tube 214 that delivers air to the system in the same general manner as described above. As explained previously, air can be heated or unheated and dehumidified and can be provided by a blower or a compressed air source. In embodiments, the air provided is through a dedicated air inlet, that is separate from the other inlets and separate from the fluid inlet. Further details of continuous seed processing system 1 can be found in United States Patent Application Publication No. 2011/0027479, which is hereby incorporated by reference.

FIG. 7 illustrates an exemplary seed stream 96.9 through a continuous feed seed treater. Seed 96 can first be fed into the apparatus at the housing inlet such that it travels through the apparatus under the influence of gravity. In a preferred configuration, the apparatus is therefore vertically arranged. After entering the housing, the seed travels into and fills metering compartments, such as slots, in the seed wheel. The seed wheel is configured to collect a predetermined quantity of seed as it rotates to ultimately dispense the seed into a seed stream. In one embodiment, the seed wheel meters the seed based on a volume of the seed. Seed wheel 206 can be rotated by a motor, such as, for example, a ⅓ horsepower variable speed motor, to dispense the seed once it has been metered and to rotatably fill each adjacent slot in the wheel. After being dispensed from the seed wheel, seed falls onto the dispersion cone. The dispersion cone dispenses the seeds generally uniformly into a curtain of treatment fluid provided by the spinning atomizer wheel. Air is delivered to the atomizer wheel with the treatment fluid via air delivery tube 214. Seeds are then ejected out of the housing outlet and can subsequently be further processor or packaged. The embodiments above are intended to be illustrative and not limiting.

The above references in all sections of this application are herein incorporated by references in their entirety for all purposes.

All of the features disclosed in this specification (including the references incorporated by reference, including any accompanying claims, abstract and drawings), and/or all of the steps of any method or process so disclosed, may be combined in any combination, except combinations where at least some of such features and/or steps are mutually exclusive.

Each feature disclosed in this specification (including references incorporated by reference, any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment (s). The invention extends to any novel one, or any novel combination, of the features disclosed in this specification (including any incorporated by reference references, any accompanying claims, abstract and drawings), or to any novel one, or any novel combination, of the steps of any method or process so disclosed The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above described aspects embodiments of the invention are merely descriptive of its principles and are not to be considered limiting. Further modifications of the invention herein disclosed will occur to those skilled in the respective arts and all such modifications are deemed to be within the scope of the invention.

The invention claimed is:

1. A seed treatment apparatus comprising:
a seed treatment containment housing having an open interior for the treatment of seed with a treatment liquid, the containment housing having a seed inlet port, a seed outlet port, and an air inlet port defined by a top cover of the containment housing;
a seed dispersion portion for distributing the seed in the open interior into an annular seed treatment region;
a seed treatment liquid input line extending through the air inlet port into the containment housing and connected to a rotating liquid dispersion portion, the liquid dispersion portion comprising a rotating tray supported and positioned in the open interior of the containment housing, the seed treatment liquid input line being connected to the rotating liquid dispersion portion at a location such that the rotating tray generates a radially outward and annular spray of the treatment liquid into the seed treatment region;
an air unit that takes ambient air and heats the ambient air to produce heated air;
a seed storage reservoir and a heater associated with the seed storage reservoir for heating the seed prior to treating the seeds; and
a duct connecting the air unit to the air inlet port defined by the top cover of the containment housing, the air inlet port being positioned such that the duct directs the heated air at the rotating tray of the liquid dispersion portion;
wherein the seed treatment liquid input line extends through a portion of the duct connecting the air unit to the air inlet port so that the seed treatment liquid input line is contacted by the heated air before the seed treatment liquid input line extends through the air inlet port defined by the top cover of the containment housing.

2. The seed treatment apparatus of claim 1 wherein contact between the heated air and the seed treatment liquid input line before the seed treatment liquid input line extends through the air inlet port causes the treatment liquid to be heated before the treatment liquid enters the containment housing.

3. The seed treatment apparatus of claim 1 further comprising a reservoir connected to the seed treatment liquid input line and a heater associated with at least one of the reservoir and the seed treatment liquid input line.

4. The seed treatment apparatus of claim 1 wherein the seed dispersion portion comprises a conical deflector.

5. The seed treatment apparatus of claim 1 wherein the seed dispersion portion is configured as a rotating bowl.

6. The seed treatment apparatus of claim 1 further comprising a dust removal port that also functions as a port for exiting the heated air that has entered the open interior of the seed treatment containment housing through the air inlet port.

7. The seed treatment apparatus of claim 1 wherein the air unit comprises an air conditioner that lowers the relative humidity of the ambient air.

8. A seed treatment apparatus comprising:
a seed treatment containment housing having an open interior for the treatment of seed with a treatment liquid, the containment housing having a seed inlet port, a seed outlet port, and an air inlet port defined by a top cover of the containment housing;
a seed dispersion portion for distributing the seed in the open interior into an annular seed treatment region;
a liquid dispersion portion supported and positioned in the open interior of the containment housing, the liquid dispersion portion comprising a rotating tray;
a duct connected to the air inlet port defined by the top cover of the containment housing;
an air conditioner that provides heated air to the duct connected to the air inlet port defined by the top cover of the containment housing, the air inlet port being located so that the duct directs the heated air directly at the rotating tray of the liquid dispersion portion;
a seed storage reservoir and a heater associated with the seed storage reservoir for heating the seed prior to treating the seeds; and
a seed treatment liquid input line extending through the air inlet port into the containment housing, the seed treatment liquid input line being connected to the liquid dispersion portion at a location such that the rotating tray of the liquid dispersion portion generates a radially outward and annular spray of the treatment liquid into the seed treatment region;
wherein the seed treatment liquid input line extends through a portion of the duct so that the seed treatment liquid input line is contacted by the heated air before the seed treatment liquid input line extends through the air inlet port defined by the top cover of the containment housing.

9. The seed treatment apparatus of claim 8 wherein contact between the heated air and the seed treatment liquid input line before the seed treatment liquid input line extends through the air inlet port causes the treatment liquid to be heated before the treatment liquid enters the containment housing.

10. The seed treatment apparatus of claim 8 further comprising a reservoir connected to the seed treatment liquid input line and a heater associated with at least one of the reservoir and the seed treatment liquid input line.

11. The seed treatment apparatus of claim 8 wherein the seed dispersion portion comprises a conical deflector.

12. The seed treatment apparatus of claim 8 wherein the seed dispersion portion is configured as a rotating bowl.

13. A seed treatment apparatus comprising:
a seed treatment containment housing having an open interior for the treatment of seed with a treatment liquid, the containment housing having a seed inlet port, a seed outlet port, and an air inlet port defined by a top cover of the containment housing;
a seed dispersion portion for distributing the seed in the open interior into an annular seed treatment region;
a liquid dispersion portion supported and positioned in the open interior of the containment housing, the liquid dispersion portion comprising a rotating tray;
an air unit that takes ambient air and heats the ambient air to produce heated air;
a duct connecting the air unit to the air inlet port defined by the top cover of the containment housing, the air inlet port being positioned such that the duct directs the heated air at the rotating tray of the liquid dispersion portion;
a seed storage reservoir and a heater associated with the seed storage reservoir for heating the seed prior to treating the seeds; and
a seed treatment liquid input line extending through the air inlet port into the containment housing, the seed treatment liquid input line being connected to the liquid dispersion portion at a location such that the rotating tray of the liquid dispersion portion generates a radially outward and annular spray of the treatment liquid into the seed treatment region;

wherein the seed treatment liquid input line extends through a portion of the duct so that the seed treatment liquid input line is contacted by the heated air before the seed treatment liquid input line extends through the air inlet port defined by the top cover of the containment housing.

14. The seed treatment apparatus of claim 13 wherein contact between the heated air and the seed treatment liquid input line before the seed treatment liquid input line extends through the air inlet port causes the treatment liquid to be heated before the treatment liquid enters the containment housing.

15. The seed treatment apparatus of claim 13 further comprising a reservoir connected to the seed treatment liquid input line and a heater associated with at least one of the reservoir and the seed treatment liquid input line.

16. The seed treatment apparatus of claim 13 wherein the seed dispersion portion comprises a conical deflector.

17. The seed treatment apparatus of claim 13 wherein the air unit comprises an air conditioner that lowers the relative humidity of the ambient air.

* * * * *